United States Patent [19]

Johnson

[11] Patent Number: 4,463,207

[45] Date of Patent: Jul. 31, 1984

[54] ARENE ALKYLATION WITH METAL OXIDE-TANTALUM HALIDE/OXIDE CATALYSTS

[75] Inventor: Thomas H. Johnson, Houston, Tex.

[73] Assignee: Shell Oil Company, Houston, Tex.

[21] Appl. No.: 535,103

[22] Filed: Sep. 23, 1983

[51] Int. Cl.³ .............................................. C07C 2/70
[52] U.S. Cl. .................................... 585/462; 585/422; 585/425; 585/431; 585/463
[58] Field of Search ............... 585/422, 425, 431, 462, 585/463

[56] References Cited

U.S. PATENT DOCUMENTS 3,728,411  4/1973  Siskin et al. .......................... 585/462
3,962,133  6/1976  Rodewald ............................ 585/462
4,116,880  9/1978  Olah .................................... 585/462

Primary Examiner—Curtis R. Davis

[57] ABSTRACT

Benzene and substituted benzene compounds are alkylated with olefins by contact with a catalyst which comprises a metal oxide substrate having tantalum (V) halide/oxide bound to the surface of the substrate.

18 Claims, No Drawings

ARENE ALKYLATION WITH METAL OXIDE-TANTALUM HALIDE/OXIDE CATALYSTS

FIELD OF THE INVENTION

This invention relates to a process for alkylating arenes, particularly benzene and substituted benzene compounds, with olefins using a catalyst comprising a metal oxide substrate having tantalum (V) halide/oxide bound to the surface.

BACKGROUND OF THE INVENTION

Alkylated aromatics are important materials that have utility for many applications. For example, the lower alkyl benzenes find frequent use as solvents as well as frequent use as chemical intermediates for the preparation of other compounds, e.g., styrenic compounds. The higher alkyl-benzenes, which are benzenes which have been alkylated with detergent range olefins are useful detergent intermediates. At present, these compounds, particularly the higher alkyl-benzenes, are manufactured by two different processes, namely, $AlCl_3$-catalyzed alkylation of aromatics with monochloro-paraffins and HF-catalyzed alkylation with internal olefins. In general, this alkylation reaction is catalyzed by strong Lewis-acid catalysts. Tantalum pentahalides have been noted as having Friedel-Crafts type of alkylation activity. Friedel-Crafts and Related Reactions, Vol. 1, G.A. Olah, Ed., Interscience, 1963, New York. The use of strong Lewis-acids such as $AlCl_3$, $BF_3$, HF and $TaCl_5$ present certain problems in their utilization for commercial applications. These materials are extremely corrosive. They are found either dissolved in or in finely particulate form in the reaction products and require expensive separation processes to maintain product purity. Many of these materials also have a tendency to isomerize both reactant olefin and alkylated arene product. An alkylation process that would utilize a Friedel-Crafts type of catalyst which would be "tied down to" an inert support would be very useful from both an environmental point of view, a product quality point of view, a handling point of view, and in alleviating corrosion of plant equipment. Further, a catalyst that would minimize isomerization reactions would aid in the production of selected products.

SUMMARY OF THE INVENTION

This invention relates to the process for alkylating arenes, particularly benzene and substituted benzenes, with olefins having the following general formula $R'CH_2=CH_2R''$, where R' and R'' are individually hydrogen or alkyl or when taken together form an alkylene group by contacting said arene with said olefin in the presence of a catalyst comprising a metal oxide substrate having tantalum (V) halide/oxide bound to the surface of said substrate.

The use of the tantalum (V) halide/oxide-metal oxide composition has several advantages over the "free" tantalum pentahalide, or other Friedel-Craft type of catalysts such as aluminum chloride or hydrogen chloride. The use of the tantalum (V) halide/oxide-metal oxide compositions in the instant process minimizes corrosion of process equipment as well as contamination of product alkylate since the tantalum halide is bound to the metal oxide substrate and does not freely move through the system. Resistance to leaching of these compositions is very good. These compositions further provide a high selectivity to mono-alkylates as well as minimize isomerization of feed olefin and alkylated product.

DESCRIPTION OF THE PREFERRED EMBODIMENTS

The preferred arene compound to be alkylated by the process of the instant invention is benzene or a substituted benzene, preferably an alkyl substituted benzene. Of the alkyl-substituted benzenes, particularly desirable are the mono- and poly- substituted lower alkyl benzenes, wherein the alkyl substituent has a carbon number ranging from 1 to about 5, more particularly ranging from 1 to about 2. Suitable examples include the following as particularly desirable feed stocks: benzene, toluene, xylenes, ethylbenzene, cumene, n-propyl benzene and other mono- and poly-lower alkyl benzenes. Particularly desirable are benzene, toluene and xylene. Other substituted benzenes having substituent groups inert to the alkylation conditions can be utilized. Typical substituents include halo, alkoxy, cyano, nitro and the like. Illustrative examples include chlorobenzene, fluorobenzene, phenol, nitrobenzene, anisole, o-hydroxyanisole, and the like. The arene feed stock can be a single aromatic hydrocarbon or a mixture of two or more aromatic hydrocarbons. The aromatic hydrocarbons can be fed into the reactor neat, or mixed in a suitable non-reactive organic solvent such as, for example, a saturated hydrocarbon.

The olefins employed in the instant alkylation process are olefins of the following general formula $$R'CH_2=CH_2R'' \qquad \qquad I$$

where R' and R'' are individually hydrogen or alkyl or when taken together form an alkylene group.

The olefins employed in the instant alkylation process can be either the lower olefins, the so-called detergent range olefins or the cyclic olefins. Thus, olefins having carbon numbers ranging from 2 to about 30, preferably from about 2 to about 20 are utilized. The olefins may be alpha- or internal olefins and may be either cyclic, straight chain or branched chain (within the confines of equation I) olefins. The olefin feed stock can be either a highly purified olefin or a mixture of two or more olefins or a fraction rich in one or more olefins and containing also paraffins or other hydrocarbons of similar boiling range.

The catalysts utilized in the process of the instant invention comprise pentavalent tantalum (also written as tantalum (V)), halogen (or halide), oxygen (or oxide) and a solid metal oxide substrate wherein at least one valence of tantalum is bound to oxygen, which oxygen is bound to the substrate, at least one valence of the tantalum is bound to halogen and the remaining tantalum valences are bound to halogen and/or oxygen, which oxygen may or may not be bound to the substrate. The halogens are fluorine, chlorine, bromine, iodine and mixtures thereof. Preferred halogens are fluorine and chlorine.

The metal oxide-tantalum (V) halide/oxide compositions used in the process of the instant invention are preferably prepared by a process comprising reacting under anhydrous conditions a suitable metal oxide substrate which has water chemically bound as hydroxyl and which is substantially free from absorbed water with tantalum pentahalide vapor and thereafter recovering the product. Thus, are produced metal oxide compositions having tantalum (V) halide/oxide bound to the surface thereof. By the term "bound" it is meant herein that the pentavalent tantalum has at least one valence bound to an oxygen which is part of the metal oxide substrate. By the term "surface" it is meant both the external and internal pore surfaces which are accessible to the tantalum pentahalide vapor during the preparation process.

The catalytic compositions utilized in the instant process basically comprise metal oxide substrates having tantalum (V) halides/oxides reactively bound to the surface of said substrate. The halides are selected from the group consisting of fluoride, chloride, bromide, iodide and mixtures thereof. Preferred halides are fluoride and chloride. The compositions are generally prepared by a process which comprises contacting the metal oxide in a substantially anhydrous state with tantalum pentahalide in the vapor state and allowing the vapor to react with the substrate in an atmosphere which is substantially oxygen- and water-free. In the preferred process, sublimation of the tantalum pentahalide is used to put the tantalum pentahalide in the vapor state. Tantalum pentachloride is the preferred sublimation agent, producing the highest metal loadings on the metal oxide substrate. The use of tantalum pentabromides, iodides or fluorides as sublimation agents produces compositions having metal loadings of less than one percent.

A variation of the above process is utilized to produce a composition containing mixed halides, particularly mixed chlorides and fluorides. In this variation, a tantalum (V) chloride/oxide-metal oxide composition is first prepared by reactive sublimation. The tantalum (V) chloride/oxide-metal oxide composition is then contacted with an oxygen-containing gas or a chemical compound containing oxygen which is weakly covalently bonded to the compound. It is postulated that oxygen replaces part of the halide of the composition. The material is then reacted with a liquid or gaseous fluorinated hydrocarbon which is believed to react preferentially with the oxygen bound only to the tantalum, producing, it is postulated, a composition containing various mixtures of chlorides, fluorides, oxides, oxychlorides, oxyfluorides, oxychlorofluorides, etc., depending on reaction conditions. Analyses of compositions prepared in this fashion show that they contain varying amounts of chlorine and fluorine along with amounts of oxygen (not bound to the substrate) ranging from insignificant to moderate, depending on the degree of fluorination obtained using the fluorinated hydrocarbon. The amount of oxygen remaining can be varied by choice of fluorinated hydrocarbon and reaction conditions. Reaction temperatures and pressures are not critical. Temperatures of room temperature or greater are generally suitable. Different fluorinated hydrocarbons will have different optimum temperatures, pressures and times of contact, and these can readily be determined by routine experimentation. Particularly suitable fluorinated hydrocarbons are the Freons, such as, for example Freon 12 ($CF_2Cl_2$), Freon 14 ($CF_4$), Freon 23 ($CHF_3$), Freon 112 ($CCl_2F$—$CCl_2F$), Freon 116 ($CF_3$—$CF_3$), Freon 142 (chlor-difluor-methyl methane), Freon C138 (octafluorocyclobutane) and similar materials. One particular advantage of this process is that it allows the preparation of compositions containing higher amounts of fluoride then does the process using reactive sublimation of tantalum pentafluoride alone. Compositions containing the fluoride are more resistant to oxygen degradation than the compositions containing chloride alone. Thus, when the mixed chloride/fluoride compositions are used as catalysts, the feeds need not be purged of oxygen and air is no longer a poison. Feeds containing oxygen (e.g., $O_2$, peroxide, etc.) however, will still compete for catalyst sites and, hence the observed rates of reaction can be reduced.

As noted above, a modification of the basic catalyst composition of the instant invention can be obtained by contacting the tantalum (V) halide/oxide-metal oxide compositions with oxygen or a compound containing oxygen which is weakly covalently bonded to said compound. Illustrative of said compounds are the peroxides and peroxy compounds, both organic and inorganic, the hypohalide's etc. It is postulated that contact of the instant compositions with oxygen or the indicated oxygen-containing compounds converts part of the halogen on the composition to oxygen which is not bound to the substrate. Thus, there are two possible types of oxygen bound to the pentavalent tantalum of the composition. One type is the oxygen(s) which is bound to the tantalum and to the substrate. This presence of this type of oxygen is required to produce the compositions of the instant invention. The other type of oxygen which optionally may be present is oxygen bound only to the tantalum of the composition. Thus, at least one valence of pentavalent tantalum is bound to oxygen which is bound to the substrate, at least one valence of the tantalum is bound to halogen and the remaining tantalum valences are bound to halogen and/or oxygen which is or is not bound to the substrate. This modification containing the optional oxygen may be effected either inadvertantly or purposefully. It may be effected by contact with oxygen or oxygen-containing compounds present as additives or impurities in feed streams when the compositions are used as catalysts. For many reactions the instant compositions provide for very active catalysts. When these very active catalysts are used in packed-bed flow reactors, they can lead to hot spots and reactor runaway. The activity of the catalyst can be moderated by contact with oxygen or oxygen-containing compounds as described above.

Tantalum (V) halides readily sublime and thus lend themselves to a preferred method of preparation which is called "reactive sublimation" wherein tantalum pentahalide(s) is sublimed into an anhydrous, non-oxidizing atmosphere and allowed to contact and thus react with the metal oxide substrate. In the preparation of these compositions by reactive sublimation, it is important that the reaction be carried out under substantially anhydrous conditions and in a neutral or reducing environment to prevent decomposition of the tantalum chloride.

In this preferred method of preparation the tantalum (V) halide is sublimed by suitable application of temperature and/or vacuum into an essentially anhydrous and oxygen-free atmosphere where it is allowed to contact and react with a substantially anhydrous metal oxide substrate. Any temperature and/or vacuum which causes the tantalum pentahalide to sublime is suitable. Temperatures to about 200° C. are suitable. Frequently the metal oxide substrate is heated during reaction, say up to about 200° C. This heating is not critical to the preparation of the catalyst, but it has been found that by so heating, a more even distribution of the tantalum halide on the metal oxide substrate is effected. After reaction, the metal oxide composition is frequently subjected to an additional period of time at sublimation conditions without the presence of a tantalum pentahalide source. This extra step allows for any unreacted tantalum pentahalide to be sublimed off of the metal oxide composition. The metal oxide substrate before use is frequently subjected to a heat treatment to remove absorbed water. Vacuum can also be applied. Generally, if this pretreatment temperature is too low, free water will remain and if the temperature is too high, sintering of the metal oxide substrate will occur, both of which will adversely affect the catalytic properties of the composition. Generally, the most desirable pretreatment temperatures of the metal oxide substrate range from about 200° to 400° C.

It is postulated that when tantalum penthalide reacts with the hydroxyl group of a metal oxide substrate, that the reaction may be illustrated variously as follows (using chloride as an illustrative halide):

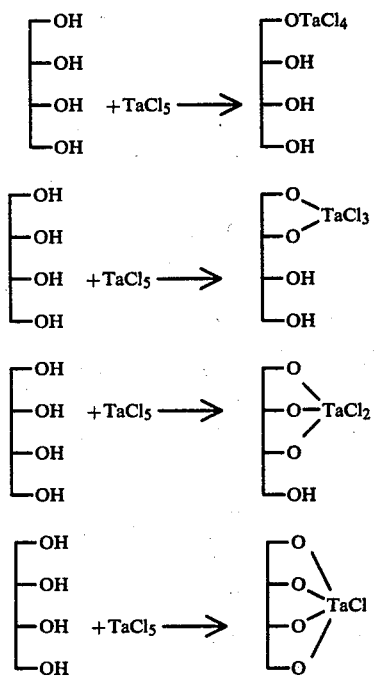

In the final composition a mixture of the above described reaction products will exist. The distribution of the products is believed to be affected by reaction conditions, such as temperature. When tantalum pentahalide is used to prepare the compositions, analysis of chlorine/tantalum ratios in composition containing about 8–17%w tantalum has shown Cl/Ta atomic ratios ranging from about 2.5:1 to about 3.5:1.

Thus, depending on the tantalum halide content desired in the final composition, a tantalum pentachloride vapor is reacted with metal oxide substrate until a part or the whole of the hydroxyl group population of the gel is exhausted.

The reaction between the tantalum pentahalide vapor and the metal oxide substate is carried out at temperatures ranging at room temperature to elevated temperatures, say 150° to 200° C. or higher. The reaction is normally carried out in an anhydrous, i.e., free from water vapor, atmosphere. The atmosphere should further be a neutral or reducing atmosphere, i.e., oxygen-free. Dispersal of tantalum pentachloride vapor in a vacuum provides a quite suitable atmosphere for reaction with the metal oxide gel.

The metal oxide-tantalum (V) halide/oxide compositions used in the instant invention may be produced in virtually any physical form, as for example, they may be pellets, beads, extrudates, microspheres and in other particular forms, as for example rings, saddles and the like, and in porous or non-porous form.

The metal oxides that are useful as substrates to prepare the catalysts used in the instant process are those inorganic oxides which have hydroxyl groups attached to the surface of the substrate. The hydroxyl groups provide the means by which the tantalum (V) pentahalides are bound to the surface of the substrate. Any metal oxide which has surface hydroxyl (or oxyhydroxyl) groups can be utilized as a substrate.

The term "metal oxide" although used herein in the singular tense, is meant to include the single oxides such as silica, or alumina as well as plural and complex oxides such as silica-alumina, silica-aluminathoria, zeolites and clays.

The preferred metal oxide substrates are the porous solid inorganic oxides which are conventionally used as catalysts and catalyst supports. Non-limiting examples of these types of materials include those having a major component of silica or alumina or both, such as, for example, alumina and aluminous materials; silica and siliceous materials; clays, particularly open lattice days; and crystalline aluminosilicates (zeolites). Non-limiting examples of aluminous and siliceous materials include, for example, silica-alumina, silica-magnesia, silica-zirconia, silica-titania, alumina-chromia, alumina-ferric oxide, alumina-titania as well as ternary compositions such as, for example, silica-aluminathoria, silica-alumina-zirconia, etc. Non-limiting examples of crystalline aluminosilicates useful as substrates include synthetic zeolites, such as, for example, A, X, Y, L and ZSM types such as ZSM-5 and others and naturally occurring zeolites, such as eriorite, faujasite, mordenite, sodalite, cancrinite and others. Non-limiting examples of open lattice clays useful as substrates include bentonite, montmorillonite and others. In a preferred embodiment, the metal oxide should have a major component of silica or aluminum or a mixture of both.

Particularly suitable as substrates are those solid inorganic oxide compositions known as metal oxide gels or gel oxides.

The gel oxides which are particularly suitable for use in preparing the catalytic compositions used in the process of the instant invention are any of the metal oxide gels that are well known in the catalytic art useful as either catalyst base materials or as promoting materials in catalyst compositions. Additionally, the term "metal oxide gel" and "gel oxide" as used herein shall also include the plural oxide gels i.e., those that contain mixtures of compounds of two or more metal oxides. A metal oxide gel is basically a metal oxide that contains chemically bound water in the form of hydroxyl groups or oxyhydroxyl groups as opposed to absorbed water and water of hydration, although absorbed water and water of hydration may also be present. They are typically prepared by the precipitation of the metal component(s) in an aqueous medium. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the composition of this invention are aluminas, silicas, alumina-silicas, aluminazirconias, silica-zirconias and the like, including naturally occurring hydrous oxide minerals such as clays such as, for example, the kaolinites, the montmorillonites and the like. Among the clays the open lattice clays are particularly desirable. Also included are the zeolites, both natural and synthetic. The structure of the gel oxides can range from amorphous to highly crystalline. Preferred oxide gel materials are selected from the group consisting of alumina, silica, alumina-silica, crystalline aluminosilicates (zeolites) and open lattice clays.

Since the tantalum (V) halide is bound to the surface of the metal oxide by a reaction of the halide with the metal oxide substrate, the metal oxide before reaction must have pendant surface hydroxyl groups attached to the surface. After reaction the metal oxide may or may not have surface hydroxyl groups, depending on the degree of reaction with the tantalum (V) halide.

Prior to use the metal oxide substrate should be substantially free of absorbed water, i.e., "substantially dehydrated or anhydrous". The absorbed or free water is removed by heating the substrate at temperatures ranging from about 100° C. to about 900° C. prior to contact with the tantalum pentachloride vapor. Any environment that provides for drying is suitable such as air, vacuum, inert gas such as nitrogen, etc. The dried substrate should be kept away from a humid atmosphere after drying. It is understood that a dried metal oxide substrate prior to use in preparing the catalysts will still contain chemically bound water in the form of hydroxide and oxyhydroxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a cogel. In fact "impurities" may be purposely added for catalytic effects. The following table lists several commercial aluminas and their properties which are found suitable.

| Alumina | Surface Area, $m^2g$ | Pore Vol., cc/gm | Na, ppm | $SO_4^=$, % wt | $Fe_2O_3$ % wt | $Cl^-$, % wt |
|---|---|---|---|---|---|---|
| CCI[a] | 252 | 0.8 | 160 | 0.06 | — | 0.02 |
| KA-209[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 51 | 0.03 | — | 0.03 |

[a]Catalysts & Chemicals, Inc., now United Catalysts
[b]Kaiser
[c]Reynolds Corp.
[d]American Cyanamid Corp.
[e]Conoco Corp.
[f]Filtrol Corp.

Silica gel is also another preferred substrate. These are readily available commercially and are essentially substantially dehydrated amorphous silica. These materials are available in various density grades, from low density with surface areas ranging from about 100–300 $m^2/g$ to regular density with surface areas up to about 800 $m^2/g$. The commercially available materials are used as dessicants, selective absorbents, catalysts and catalyst supports. Regarding purity of the silica, it may be stated that small amounts of impurities are not generally detrimental and may be beneficial when the impurity is present as a co-gel. In fact, "impurities" may be purposely added for catalytic effects. The following table lists several commercial silicas and their properties which are found suitable.

| Support | Surface Area, $m^2/g$ | Pore Vol, cc/g | Density g/cc | Particle Size |
|---|---|---|---|---|
| Davison* Grade 952 $SiO_2$ | 300 | 1.65 | 0.35 | 70 mesh (avg) |
| Davison Grade 59 $SiO_2$ | 300 | 1.15 | 0.38 | 8 mesh |
| Davison Grade 57 $SiO_2$ | 300 | 1.0 | 0.4 | 100 mesh |
| Davison Grade 12 $SiO_2$ | 700 | 0.54 | 0.75 | 20 mesh |
| Davison Grade 03 $SiO_2$ | 750 | 0.43 | 0.7 | 8 mesh (avg) |

*Manufactured by Davison Chemical Div., W. R. Grace & Co.

Other preferred substrates are the aluminosilicates. These materials contain various mixtures of aluminum and silicon oxides. They are readily available commercially and are generally employed as cracking catalysts. Typically they contain from about 50 to about 95, preferably from about 70 to about 90 percent by weight of silica. Illustrations of commercially available aluminasilicas are Davison Grade 980-25 (manufactured by Davison Chemical Division, W. R. Grace & Co.) which contains about 75% $SiO_2$ and 25% $Al_2O_3$ and Davison Grade 980-13 which contains about 87% $SiO_2$ and 13% $Al_2O_3$. These materials can be prepared in a conventional fashion, as for example by co-precipitation, co-gellation, or by spray drying.

Encompassed within the term "aluminosilicates" are most of the zeolites. The zeolites are found to be specifically useful as substrates. Zeolites are ordered, porous crystalline aluminosilicates having a definite crystalline structure within which there are a large number of small cavities which are interconnected by a number of still smaller channels. Zeolites useful as substrates may be either synthetic or natural. At least 34 species of zeolite minerals are known and the synthetic zeolites number in the hundreds. Any zeolite will be useful as a substrate provided that the zeolite, prior to reaction with tantalum pentahalide, contains chemically bound water in the form of hydroxyl groups. Depending on the state of reaction, the reacted product may contain no hydroxyl groups if all such groups were reacted with the tantalum pentahalide, or there may be unreacted hydroxyl groups still present.

Further descriptions of the preparation of the catalysts used in the instant process are found in application Ser. No. 527,535, filed Aug. 29, 1983, incorporated by reference herein.

The tantalum pentahalides utilized to prepare the compositions used in the process of the instant invention are readily obtainable commercially.

The compositions utilzed as catalysts in the instant invention are used in typical fashion, for example, in packed beds or in fluidized beds. In operation, a process stream containing benzene or a substituted benzene to be alkylated is combined with a process stream containing an olefin to be utilized for alkylation and passed over a catalyst bed at a temperature ranging from about 0° C. to about 450° C., preferably from about 0° C. to about 250° C. and a pressure ranging from about 0.1 to about 1000 atm. An aromatic to olefin feed ratio (molar) of about 5 to about 1 or greater is typically preferred to obtain high monoalkylate selectivity. Lower ratios do not affect conversion but will give lower monoalkylate selectivity.

Upon completion of the reaction, the product obtained can be separated into its individual components of product, by-product and reactant by simple means, such as for example, by distillation.

The catalysts described herein, when utilized in the process of the instant invention provide distinct advantages over the use of unsupported materials such as tantalum pentachloride. The catalysts are heterogeneous and can readily be separated from reaction products. The described catalysts are very resistant to leaching, thus, minimizing product contamination and further minimizing corrosion of plant equipment. The described catalysts also provide for an enhanced conversion to a mono-alkylated product when compared to conventional catalysts. As used herein, the term "mono-alkylated product" refers to a product prepared from a given arene by adding one alkyl group to the benzene ring. The mono-alkylated product would thus have one more alkyl group than the starting material. For example, when the starting material was a xylene, the mono-alkylated product would be a trialkylbenzene. The described catalyst also provide for an enhanced selection to the 2-substituted alkane product when compared to competitive products.

The instant process thus comprises an improved process for alkylating benzene and substituted benzenes with olefins by contacting said benzene or substituted benzene and said olefins with a catalyst composition comprising a metal oxide substrate having tantalum (V) halide/oxide bound to the surface of the substrate.

The process of the instant invention and the preparation of the compositions used as catalysts in the instant invention will be further described below by the following illustrative embodiments which are provided for illustration and are not to be construed as limiting the invention.

ILLUSTRATIVE EMBODIMENTS

Catalyst Preparation

A. The following illustrates the preparation of a catalyst composition which is utilized in the instant invention. A 200-ml Schlenk flask containing 50-75 g of silica gel (Davison 57, 60-100 mesh) was heated to 300° C. under a vacuum of ca. 0.1 torr for 16-20 h. The flask was moved into a dry box whereupon 6.5 g of the silica was placed on one side of a fritted Schlenk tube. Tantalum chloride (6.0g) was placed on the other side of the frit. The $TaCl_5$ end of the tube was wrapped with heating tape and then an insulation wrap was installed along with a Thermocouple wire. A vacuum of ca. 0.1 torr was applied at the end of the silica-containing section. The deposition was carried out overnight (16-20 h) at 150° C. with the tube mounted horizontally. The siliceous material was removed in a dry box and then subjected to a vertical sublimation in order to remove any condensed but unreacted $TaCl_5$.

B. The following technique is been found to result in a some-what more homogeneous catalyst then the above described technique and is utilized where uniformity is important. In this preparative technique a glass scrubbing bottle was modified by internally adding a coarse fritted disc which divided the bottom into an upper section and a lower section. The lower section was fitted with a stoppered connection which allowed it to be charged with tantalum pentachloride and the upper section was fitted with a vacuum stopcock connection which allowed it to be closed off or to be connected to a vacuum. To the modified gas-scrubbing bottle were added about 20 g of $TaCl_5$ to the bottom section and about 60 g of Davison 57 silica ($-20+30$ mesh, pretreated at 300° C. under 0.1 torr vacuum for 12-24 h) to the top section. Both sections were loaded in a dry box containing a nitrogen atmosphere. The bottom section was stoppered and the top section had the vacuum stopcock closed before removing from the dry box. The bottom section of the bottle was immersed into an oil bath and heated at about 150° C. The top section was wrapped with heating tape and heated to about 150° C. A vacuum (ca 0.1 torr) was applied at the top of the bottle. The heating and vacuum phase of the preparation was simultaneous and carried out over a period of 18 h. At the end of 18 h, the bottle (vacuum stopcock closed) was put back into the dry box and 20 g a fresh $TaCl_5$ was added to the bottom section. The rest of the procedure was then repeated for another 18 h. Then the silica was removed, in a nitrogen-filled dry box, and vertically sublimed at 150° C. and 0.1 torr for 18 h. This step was employed to remove any deposited but unreacted $TaCl_5$ on the silica surface. A small (<200 mg) of $TaCl_5$ was generally collected on the cold finger of the sublimator.

C. In a variation of the process just described above 24 milliliters of the tantalum (V) chloride-silica composition was added directly to a flow reactor and then subjected to an air flow at 200° C., 100 psi at a GSHV of 10,000 $h^{-1}$ for 30 minutes. Then, $CF_4$ (Freon 14) was passed through the bed at 200° C., 100 psi and a GHSV of 240 $h^{-1}$ for a period of 2 hours. Analysis of the resultant composition of the instant invention by neutron activation showed it to contain about 15.7 %w Ta, 3.6% Cl and 0.40% w F.

D. In another variation of the just described process, 12 milliliters of the tantalum (V) chloride-silica composition was added to a fixed-bed flow reactor and treated with air at a flow rate of 4 l/min for 15 minutes at 100 psi and 200° C. The air-treated material was then treated with Freon 12 ($CF_2 Cl_2$) at 200° C. and 70 psi at a flow rate of 2.4 l/hr for 5 hours. The flow tube was then sealed and left under an atmosphere of Freon 12 at 200° C., 75 psi for 60 hours. Analysis of the resultant composition of the instant invention by neutron activation showed it to contain about 15.7 %w Ta, 1.9 %w Cl and 5.7 %w F.

PROCESS

A. Alkylation of benzene with lower olefins.

The following examples illustrate the alkylation of benzene with a lower molecular weight acyclic olefin.

In a dry box, to a 50-ml Erlenmeyer flask containing a stirring bar were added 10-ml of benzene, 0.5-ml of 1-pentene, 0.5-ml of iso-pentane (as an internal standard), 1 g of a silica-tantalum chloride composition prepared as described above (preparation A, Davison Grade 57 silica) and containing 14.4 wt% of tantalum. The reaction was stirred at ambient temperature under ambient atmospheric pressure for 30 minutes. The reaction product was then filtered, and the solution analyzed directly. Analysis of the product showed almost complete conversion of the 1-pentene with a 99+% selectivity to pentyl benzene.

The above experiment was repeated using 5 ml of benzene, 1 ml of 2-pentene, 1 ml of iso-pentane and 0.25 g of a silica-tantalum (V) chloride composition (2 mol % metal concentration basis initial 2-pentene used) described above (preparation A, Davison Grade 57 silica). Analysis of the reaction product at various time intervals gave the following results:

TABLE I

| Time, min | 2-isomer[a] / 3-isomer | % [b] Conversion | % [c] Selectivity |
|---|---|---|---|
| 30 | 3.7 | 64 | 97 |
| 60 | 3.6 | 83 | 91 |
| 90 | 3.8 | 99 | 90 |
| 120 | 3.8 | 100 | 90 |

[a] ratio of 2-phenylpentane to 3-phenylpentane
[b] based on 2-pentene
[c] selectivity to pentylbenzenes (monoalkylate)

For comparative purposes, the immediate proceeding experiment was repeated using $TaCl_5$ and $AlCl_3$ as catalysts in amounts sufficient to provide 2 mol % metal basis initial 2-pentene. The results are shown below:

| Catalyst | Time, min | 2-isomer[a] / 3-isomer | % [b] Conversion | % [c] Selectivity |
|---|---|---|---|---|
| $TaCl_5$ | 30 | 3.1 | 99 | 59 |
| $TaCl_5$ | 60 | 3.1 | 100 | 55 |
| $AlCl_3$ | 30 | 2.9 | 100 | 51 |

[a] ratio of 2-phenylpentane to 3-phenylpentane
[b] based on 2-pentene
[c] based on pentylbenzenes (monoalkylate)

As can be see above, the tantalum (V) chloride-silica composition provides a higher selectivity to pentylbenzene with higher selectivity to the 2-phenylpentane isomer than do the $TaCl_5$ and $AlCl_3$ catalysts. Further, these latter catalysts produce all the problems associated with unsupported catalysts.

A number of catalysts were prepared using different silica and silica-alumina substrates. These were tested for the alkylation of benzene with 1-pentene. The reactions were run using 2 mol % tantalum with a benzene/1-pentene ratio of 6/1 (mol/mol) at room temperature for 30 minutes. The results are shown in Table II below:

TABLE II

| Support (Grade)[a] | Surface Area, $m^2/g$ | Ta, % w[b] | Conversion, % [c] | Selectivity, % [d] | 2-PP/ 3-PP[e] |
|---|---|---|---|---|---|
| $SiO_2$ (57) | 300 | 8.9 | 100 | 90 | 3.8 |
| $SiO_2$ (59) | 300 | 9.0 | 100 | 90 | 3.7 |
| $SiO_2$ (12) | 700 | 9.4 | 100 | 80 | 3.5 |
| $SiO_2$ (3) | 750 | 0.7 | <5 | <70 | — |
| $SiO_2$—$Al_2O_3$ (980-25)[f] | 325 | 8.8 | 80 | 71 | 2.9 |

[a] Davison Grade.
[b] Amount of tantalum found in the catalyst sample.
[c] Based on 1-pentene.
[d] Based on monoalkylate.
[e] Ratio of 2-phenylpentane to 3-phenylpentane.
[f] 25% $Al_2O_3$.

B. Alkylation of Benzene with Higher Olefins

The following example illustrates the alkylation of benzene with a higher molecular weight acyclic olefin.

In a dry box, to a 50-ml Erlenmeyer flask containing a stirring bar were added 10 ml of benzene, 0.5 ml of olefin (listed in Table III), and about 0.4 gms of a silica-tantalum (V) chloride composition prepared as described above (preparation A, Davison Grade 57 Silica) and containing 14.4 %wt of tantalum (4 mol % basis olefin). The reaction was stirred at room temperature and atmospheric pressure for 30 minutes. The reaction product was filtered and the solution analyzed. The results are shown below:

TABLE III

| Olefins | 1-Dodecene | Internal Dodecene[c] | C-11, C-12 Internal Olefins[d] |
|---|---|---|---|
| Conversion % [a] | 100 | 70 | 64 |
| Selectivity % [b] | 99 | 99 | 99 |
| 2-isomer | 49 | 27 | 30 |
| 3-isomer | 20 | 18 | 14 |
| 4-isomer | 12 | 15 | 18 |
| 5 + 6 isomer | 19 | 40 | 38 |

[a] Conversion after 30 minutes
[b] Selectivity for monoalkylate
[c] A Thermodynamic mixture of internal dodecenes
[d] C-11 and C-12 values were averaged. The C-11, 12 feed is a mixture of internal olefin isomers. Sample is 55% $C_{11}$ and 45% $C_{12}$ olefins.

From the above data, it can be seen that selectivity for the 2-position is dominant. For 1-dodecene, the selectivity in the 2-position is 49%. This compares favorably to know catalyst systems. For example, the percent of 2-phenyldodecane obtained using HF, $AlCl_3$, and $H_2SO_4$ was 20, 32 and 41% (A. C. Olson, Ind. Eng. Chem. 52, 833 (1960)).

A fixed-bed flow reactor was set up to illustrate the use of a flow reactor in the instant process and compare it with the results for the batch reaction described above.

A ten to one mole ratio of benzene to 1-dodecene was feed into a down flow, fixed-bed reactor at a liquid hourly space velocity of about 0.5 $h^{-1}$ over a silica-tantalum chloride catalyst (−20+30 mesh, 10.4 wt% tantalum, as per preparation B above) at a pressure and temperature of about 100 psi and 100° C., respectively. Under these conditions 100% of the dodecene was converted with 98% selectivity to monoalkylate. The majority of the remaining 2% was dialkylate (no trialkylate was observed). The product contained 40% of the 2-isomer, 22% of the 3-position isomer, 13% of the 4-position isomer and 25% of the 5+6-position isomers. The selectivity for the 2-position of the dodecene chain is some what lower in the flow reactor than in the batch reactor but it is still quite high. However, the flow reactor was operated at a higher temperature (100° C.) than the batch reactor (25° C.), and it would be expected that the positional selectivity of the two processes would differ somewhat.

C. Alkylation of Benzene with Propylene to Produce Cumene

Cumene is an important chemical intermediate which is utilized principally to make phenol. The efficiency of the phenol process is thus closely tied into the efficiency of a cumene process. In this example a silica-tantalum chloride catalyst is utilized to demonstrate its efficiency in a flow reactor to prepare cumene from benzene and propropylene.

Into a fixed-bed, upflow reactor were charged 4.8 grams of silica-tantalum chloride catalyst (20+30 mesh, 15.4 wt% tantalum, prepared (as per preparation B above) on Davison 57 silica having a surface area of 300 $m^2/g$ surface area and 1.0 cc/gram pore volume). The feed was benzene/probane/propylene in a 7.5:2:1 mole ratio. A weight hourly space velocity of 30 $h^{-1}$ and temperature and pressure of 100° C. and 150 psi were utilized respectively. Results are shown in Table IV.

TABLE IV

| Reaction Time, hours | Propylene Conversion mol % | Cumene[a] Selectivity mol % | Diisopropyl[b] Benzene sel mol % | Triisopropyl[c] Benzene sel mol % |
|---|---|---|---|---|
| Initial (<1 hr) | 100 | 92 | 7 | <1 |
| 1 | 100 | 91 | 8 | <1 |
| 2 | 100 | 92 | 7 | <1 |
| 3 | 100 | 93 | 6 | <1 |
| 4 | 100 | 94 | 5 | <1 |
| 5 | 100 | 92 | 7 | <1 |
| 25 | 100 | 92 | 7 | <1 |
| 79 | 100 | 92 | 7 | <1 |
| 70 | 100 | 92 | 7 | <1 |

[a] ±1%
[b] ±2%
[c] Barely detectable

The above example was repeated using various reaction conditions. These results are shown in Table V.

TABLE V[a]

| Temp. °C. | Pressure, psi | WHSV hours$^{-1}$ | Benzene Propylene Ratio (molor) | Propylene Conv. mol % | Cumene[b] Sel. mol % | Diisopropyl[c] Benzene Sel. mol % |
|---|---|---|---|---|---|---|
| 100 | 150 | 30. | 7.5 | 100 | 92 | 7 |
| 100 | 150 | 30 | 16.5 | 100 | 96 | 4 |
| 100 | 100 | 30 | 3.8 | 100 | 88 | 10 |
| 150 | 100 | 15 | 10.3 | 100 | 86 | 10 |
| 150 | 100 | 5 | 10.3 | 100 | 82 | 12 |
| 200 | 300 | 30 | 7.5 | 100 | 92 | 6 |
| 175 | 150 | 30 | 7.5 | 100 | 93 | 6 |

[a] All reactions were carried out in the upflow mode measurements were taken after 5 residence times. In all of the above examples, the feeds also contained propane. Although propane is not required for reaction, it is usually added intentionally in most industrial cumene facilities. The propane/propylene ratio was 2:1(m) in all cases.
[b] ±1%
[c] ±2%

The tantalum content of the product stream was analyzed and found to range from about 0.34 to about 0.84 ppm with an average of about 0.6. This is an extremely low tantalum impurity content and indicates that the catalysts would have a very long life.

The above data indicates several benefits that could obtained using the silica-tantalum chloride catalyst. For example the catalysts operates under extremely mild conditions compared to conventionally utilized catalysts. Even at room temperature, conversion is almost a 100%. The catalyst is extremely active. At the relatively high rate of a weight hourly space velocity of about 30, conversions were also 100%. Furthermore, a particularly undesirable by-product, n-propylbenzene (NPB), which is found in commercial cumene processes, is extremly low in the instant process. At 100° C. the NPB content was 29 ppm. With increasing temperature, one obtains higher NPB content. Thus at 150° C. and 175° C., the NPB content was 94 and 252 ppm, respectively. A comparison of the instant process and a commercial process utilizing phosphoric acid on Kieselguhr is illustrated in Table VI.

TABLE VI

|  | H$_3$PO$_4$/ Kieselguhr | Silica-Tantalum (V) Chloride |
|---|---|---|
| Temperature, °C. | 200-250 | 100 |
| Pressure, psi | 500 | 150 |
| Benzene/propylene, m/m | 8-10/1 | 7.5/1 |
| WHSV, h$^{-1}$ | 1-2 | 30 |
| Conversion of Propylene, % | 100 | 100 |
| Selectivity to Cumene, % | >90 | >90 |
| n-propylbenzene, ppm | 150-260 | 29 |

Into a fixed-bed, upflow reactor were charged 5.7 grams of silica-tantalum chloride/fluoride catalyst (prepared on 1.5 mm silica spheres, with a surface area of 350 m$^2$/g, a pore volume of 1.4 cc/g and a density of 0.35, using preparation C above and employing Freon 12 as the fluorinating agent; 12 wt% tantalum). The feed was benzene/propylene (8:1, m), A weight hourly space velocity of 30 h$^{-1}$ and a pressure of 500 psi were employed. A Three-zone furnace was used to heat the reactor and the temperature (case I) of the lower, middle and upper zones were 100°, 145°, 190° C., respectively. In case II, the temperatures were 195°, 205° and 225° C., respectively. The reactor system was allowed 10 residence times to line our before measurements were taken. In case I, the propylene conversion was 80% and the selectivities (molar) to cumene, dissopropylbenzene (DIPB), and triisopropylbenzene were 81.4, 16.1 and 2.5%, respectively. In case II, the propylene conversion was 85% and the selectivities (molar) were 81.7, 15.9, and 2.4%, respectively.

D. Alkylation of Benzene with Cyclohexene to Produce Phenylcyclohexane

Phenylcyclohexane is another chemical intermediate used to produce phenol with a cyclohexanone by-product. The cyclohexanone by-product can be reduced and dehydrated to cyclohexene which then can be utilized to alkylate benzene to produce more of the starting intermediate. This process avoids the preparation of acetone as a by-product as is the case when cumene is utilized to product phenol. This example illustrates the use of a silicatantalum (V) chloride/oxide catalyst to alkylate benzene with cyclohexene to produce phenylcyclohexane.

In a dry box, to a 50-ml Erlenmeyer flask containing stirring bar were added 10 ml of benzene, 1 ml of cyclohexene, and 0.5 gram of a silica-tantalum chloride/oxide composition prepared as described above (preparation B, Davison Grade 57 silica) and containing 9.6 wt% of tantalum. The reaction was stirred at ambient temperature under atmospheric pressure for about 60 minutes. The reaction product was filtered and the solution was analyzed. The conversion of cyclohexene was about 100% with a selectivity to phenylcyclohexane of 98%. The other 2% of product was cyclohexene dimer. No 1-methyl-1-phenylcyclopentane was observed. Commercial catalysts such as phosphoric acid/Kieselguhr and the aluminum-based catalysts give a large amount of the ring contracted 1-methyl-1-phenylcyclopentane by-product in addition to the desired phenylcyclohexane. HF and H$_2$SO$_4$ give lesser amounts of the ring contracted by-product but give poorer selectivity to the desired product when compared to the silica-tantalum (V) chloride/oxide composition utilizing the instant invention.

E. Alkylation of O-Xylene with Higher Alkanes

Alkyl xylenes are readily convertible to alkyl xylene sulphonates which have utility in enhanced oil recovery applications. Alkylation of o-xylene can produce a 1,2-dimethyl-3-alkyl xylene and/or a 1,2-dimethyl-4-alkyl xylene with respect to substitution around the ring in addition to attachment of the xylyl group at different carbon atoms along the alkyl chain. Different isomer mixes produce different properties.

In a dry box to a 50-ml Erlenmeyer flask containing a stirring bar were added 8.5 ml of o-xylene, 1.5 ml of either 1-dodecene or a mixture of $C_{12}$ olefin (listed in Table VI) and 0.6 grams of a silicatantalum chloride composition prepared as described above (preparation A, Davison Grade 57 silica) and containing 8.7 %wt of tantalum (4 mole % basis olefin). The reaction was stirred at room temperature and atmospheric pressure for 1 hr. The reaction was filtered and the solution analyzed. The results are shown in Table VI.

TABLE VI

| Olefin | Olefin Conv. mol. % | Selectivity (1,2,3-Isomer), mol. %[b] | | | |
|---|---|---|---|---|---|
| | | 1,2,3-isomer | 2-isomer | 3-isomer | 4 + 5 + 6 isomer |
| 1-Dodecene | 98 | 29 | 61 | 25 | 14 |
| $C_{11}$,$C_{12}$ Internal Olefins[a] | 98 | 24 | 21 | 25 | 54 |

| | Selectivity (1,2,4-Isomer), mol % | | | |
|---|---|---|---|---|
| | 1,2,4-isomer | 2-isomer | 3-isomer | 4 + 5 + 6 isomer |
| 1-Dodecene | 71 | 58 | 21 | 21 |
| $C_{11}$,$C_{12}$ Internal Olefins[a] | 76 | 16 | 21 | 63 |

[a]A Thermodynamic mixture of internal olefins. Sample is 55% $C_{11}$ and 45% $C_{12}$ olefins. Values for $C_{11}$ and $C_{12}$ are averaged.
[b]1,2,3-isomer represents 1,2-dimethyl-3-alkylbenzene; 2-isomer, 3-isomer represent xylyl substitutions on 2-position, 3-position, etc. of alkyl group.

E. Alkylation of Anisole with 1-Dodecene

In a dry box, to a 50-ml Erlenmeyar flask containing a stirring bar were added 10 ml of anisole, 1 ml of 1-dodecene and 0.5 g of the silica-tantalum chloride composition prepared as described above (preparation B, Davison Grade 57 silica) and containing 9.6 wt% of tantalum.

The reaction was stirred at ambient temperature under atmospheric pressure for 30 minutes. The reaction was filtered and the solution analyzed. Analysis of the product showed a 1-dodecene conversion of 100% with a 98% selectivity to methoxyalklbenzene monoalkylate isomers.

F. Alkylation of Chlorobenzene with 1-Dodecene

In a dry box, to a 50-ml Erlenmeyer flask containing a stirring a stirring bar were added 10 ml of chlorobenzene, 1 ml of 1-dodecene and 0.5 g of the silica-tantalum chloride composition prepared as described above (preparation B, Davison Grade 57 silica) and containing 9.6 wt% of tantalum. The reaction was stirred at ambient temperature under atmospheric pressure for about 30 minutes. The reaction product was then filtered and the solution analyzed directly. The analysis of the product showed a conversion of 1-dodecene of about 80% with a selectivity of about 98% to alkylchlorobenzene monoalkylate isomers.

G. Alkylation of Phenol with 1-Dodecene

A fixed-bed flow reactor containing 12 cc of the silica-tantalum chloride composition prepared as described above (preparation B, Davison Grade 57 silica) and containing 14 wt% tantalum was treated with a mixture of phenol and cyclohexane (1:5 v/v) at a LHSV of 1 h$^{-1}$ at 100° C. and 400 psi for 2 h. A KOH trap was attached after a liquid trap on the exit stream to entrap HCl by-product. A feed stream containing 1-dodecene, phenol, and cyclohexane (5:1:4, m) was then fed at a LHSV of 1 h$^{-1}$ at 100° C. and 400 psi. Phenol conversion was approximately 35% with a selectivity to dodecylphenol of greater than 90%. No dodecylphenyl ether was observed.

I claim:

1. A process for alkylating benzene and substituted benzenes with an olefin having the general formula, R'CH$_2$=CH$_2$R", where R' and R" are individually hydrogen or alkyl or when taken together form an alkylene group, which process comprises contacting said benzene or substituted benzene with said olefin at a temperature ranging from about 0° C. to about 450° C. with a catalyst comprising pentavalent tantalum, halogen, oxvgen and a metal oxide substrate wherein at least one valence of tantalum is bound to oxygen which is bound to the substrate, at least one valence of tantalum is bound to halogen and the remaining tantalum valences are bound to halogen and/or oxygen which may or may not be bound to the substrate.

2. The process of claim 1 wherein said substrate is silica, alumina, silica-alumina, zeolite, open lattice clay or mixtures thereof and the halogen is chloride or fluoride or mixtures thereof.

3. The process of claim 1 wherein said substrate has a major component of silica or alumina or a mixture thereof and the halogen is chloride or fluoride or a mixture thereof.

4. The process of claim 1 wherein the pressure ranges from about 0.1 to about 1000 atmospheres.

5. The process of claim 1 or 4 wherein the olefin has a carbon number ranging from 2 to about 30.

6. The process of claim 1 wherein the olefin has a carbon number ranging from about 2 to about 10.

7. The process of claim 1 wherein the olefin has a carbon number ranging from about 10 to about 30.

8. The process of claim 1 wherein the substituted benzene is substituted with an alkyl group of 1 to about 5 carbon atoms.

9. The process of claim 8 wherein the alkyl group has 1 to about 2 carbon atoms.

10. A process for alkylating benzene with propylene to produce cumens which process comprises contacting said benzene with propylene at a temperature ranging from about 0° C. to about 450° C. with a catalyst comprising pentavalent tantalum, halogen, oxygen and a metal oxide substrate wherein at least one valence of tantalum is bound to an oxygen which is bound to the substrate, at least one valence of tantalum is bound to halogen and the remaining tantalum valences are bound to halogen and/or oxygen which may or may not be bound to the substrate.

11. The process of claim 10 wherein said metal oxide is silica, alumina, silica-alumina, zeolite, open lattice clay or mixtures thereof and the halogen is chloride or fluoride or mixtures thereof.

12. The process of claim 10 wherein said metal oxide has a major component of silica, or alumina or a mixture thereof and the halogen is chloride or fluoride or mixtures thereof.

13. The process of claim 10 wherein the pressure ranges from about 0.1 to about 1000 atmospheres.

14. A process for alkylating benzene with cyclohexene to produce phenyl cyclohexane which process comprises contacting said benzene with cyclohexene at a temperature ranging from about 0° C. to about 450° C. with a catalyst comprising pentavalent tantalum, halogen, oxygen and a metal oxide substrate wherein at least one valence of tantalum is bound to oxygen which is bound to the substrate, at least one valence of tantalum is bound to halogen and the remaining tantalum valences are bound to halogen and/or oxygen which may or may not be bound to the substrate.

15. The process of claim 14 wherein said metal oxide is silica, alumina, silica-alumina, zeolite, open lattice clay or mixtures thereof and the halogen is chloride or fluoride or mixtures thereof.

16. The process of claim 14 wherein said metal oxide has a major component of silica, or alumina or a mixture thereof and the halogen is chloride or fluoride or mixtures thereof.

17. The process of claims 1, 10 or 14 wherein the catalyst is prepared by a process which subliming tantalum pentachloride and reacting in a substantially and oxygen-free atmosphere the vapor therefrom with a anhydrous, hydroxyl-containing metal oxide substrate.

18. The process of claims 1, 10, or 14 wherein the catalyst is prepared by a process which comprises:
(a) subliming tantalum pentachloride and reacting in a substantially anhydrous and oxygen-free atmosphere the vapor therefrom with a substantially anhydrous, hydroxyl-containing metal oxide substrate,
(b) contacting the product of step (a) with an oxygen-containing gas and,
(c) contacting the product of step (b) with a liquid or gaseous fluorinated hydrocarbon.

* * * * *